US005312349A

United States Patent [19]
Löhn

[11] Patent Number: 5,312,349
[45] Date of Patent: May 17, 1994

[54] MEDICAL TREATMENT DEVICE, IN PARTICULAR FOR SURGICAL PURPOSES

[75] Inventor: Gerd Löhn, Biberach an der Riss, Fed. Rep. of Germany

[73] Assignee: Kaltenbach & Voigt GmbH & Co., Biberach an der Riss, Fed. Rep. of Germany

[21] Appl. No.: 981,365

[22] Filed: Nov. 25, 1992

[30] Foreign Application Priority Data

Nov. 25, 1991 [DE] Fed. Rep. of Germany ....... 4138673

[51] Int. Cl.⁵ ............................ A61F 7/12; H05B 7/12
[52] U.S. Cl. ....................................... 604/113; 433/82; 433/126
[58] Field of Search ............... 604/113, 150, 151; 606/170, 171, 180; 433/82, 84, 85, 87, 88, 114–117, 126–129, 131

[56] References Cited

U.S. PATENT DOCUMENTS

| | | | |
|---|---|---|---|
| 3,789,506 | 2/1974 | Johns | 433/126 |
| 4,321,039 | 3/1982 | Schuss et al. | 433/126 |
| 4,353,697 | 10/1982 | Nakanishi | 433/126 |
| 4,484,891 | 11/1984 | Nash | 433/116 |
| 4,642,738 | 2/1987 | Meller | 433/114 X |
| 4,802,852 | 2/1989 | Shea | 433/128 X |
| 4,957,483 | 9/1990 | Gonser et al. | 433/126 X |
| 4,975,058 | 12/1990 | Woodward | 433/126 |
| 5,039,304 | 8/1991 | Heil | 433/126 |

FOREIGN PATENT DOCUMENTS 2508790 9/1976 Fed. Rep. of Germany .
3412969 10/1984 Fed. Rep. of Germany .

Primary Examiner—John D. Yasko
Assistant Examiner—Frank Wilkens
Attorney, Agent, or Firm—Scully, Scott, Murphy & Presser

[57] ABSTRACT

A medical treatment device, in particular for surgical purposes, having at least one treatment instrument in the form of a hand piece which can be connected to a control unit by means of a flexible supply line, there being associated with the treatment device, preferably with the control unit, a source of treatment agent, in particular for cooling fluid, to which it is possible to connect a treatment agent line, which extends at least in part through the supply line to the front end of the hand piece, in the form of a hose, the treatment agent line having a hose section which extends with radial play for movement in the supply line as far as the hand piece and is there connected to a plug-in spigot which is plugged in a releasable manner in an axial plug-in socket in the hand piece and has an axial and a radial channel section, of which the axial channel section issues from the hose connection and the radial channel section is connected to the continuing treatment agent line.

14 Claims, 3 Drawing Sheets

MEDICAL TREATMENT DEVICE, IN PARTICULAR FOR SURGICAL PURPOSES

TECHNICAL FIELD OF THE INVENTION

The invention relates to a medical treatment device, in particular for surgical purposes.

BACKGROUND OF THE INVENTION AND PRIOR ART

In the treatment of the human or animal body with a medical treatment instrument, in many cases it is necessary to add a gaseous or, in particular, fluid treatment agent, which can be air, water or a mixture thereof (spray). In many cases, in particular in surgical and microsurgical treatment, a cooling fluid is required, in which case it is usual to use a salt solution (NaCl).

The treatment agent is fed to the treatment instrument through a flexible tube line, in particular a hose line. It has already been proposed to arrange the flexible tube line on or in the supply line. On account of it hollow construction, the flexible tube line is sensitive to severe bending, something which often cannot be precluded during the treatment. The life of such a flexible tube line can therefore be reckoned to be shorter than other lines, for example, electric cables. If a defective flexible tube line is exchanged, the supply line itself can therefore be used further.

In particular after surgical treatment, sterilization not only of the treatment instrument, but also of the supply line fixedly connected therewith is necessary, this occurring in many cases by means of steam pressure sterilization. The strength and life of the flexible tube line are impaired in particular as a result of this thermal stressing.

In particular when a mineral solution, such as for example a salt solution, is used as a cooling fluid, there is then the danger of crystallization and deposits in the flexible tube line which can diminish the latter's free cross section or even block it and thus can impair the cooling. This danger is greater the smaller the cross section of the flexible tube line. Removal of the flexible tube line from the supply line is not possible in the case of the known treatment devices without unjustifiable effort or expense.

It has also already been proposed to guide the flexible tube line in the end region of the supply line remote from the treatment instrument substantially radially out of this region and thus, by by-passing the plug-in connection for the supply line, be able to connect it to the available treatment agent source or pump respectively.

OBJECT OF THE INVENTION

The object of the invention is to develop a treatment device of the kind specified at the beginning so that the flexible tube line can be removed and installed or exchanged with little effort or expense.

SUMMARY OF THE INVENTION

According to the present invention there is provided a medical treatment device, in particular for surgical purposes, having at least one treatment instrument in the form of a hand piece which can be connected to a control unit by means of a flexible supply line, there being associated with the treatment device, preferably with the control unit, a source of treatment agent, in particular for cooling fluid, to which it is possible to connect a treatment agent line, which extends at least in part through the supply line to the front end of the hand piece, in the form of a hose, wherein the treatment agent line has a hose section which extends with radial play for movement in the supply line as far as the hand piece and is there connected to a plug-in spigot which is plugged in a releasable manner in an axial plug-in socket in the hand piece and has an axial and a radial channel section, of which the axial channel section issues from the hose connection and the radial channel section is connected to the continuing treatment agent line.

In the treatment device according to the invention, the flexible tube line is secured with clamping, in the sense of a fitting, and thus so as to be tight on a preferably pin-shaped fitting portion, only in its front end region, whilst it is received in its remaining region in the supply line with play for movement. The fitting portion itself is likewise held in a plug-in socket in the treatment instrument and in particular can be drawn out towards the front with the flexible tube line. The installation of the flexible tube line can be effected by insertion from the front, something which can be carried out easily and quickly, because the plug-in socket of the fitting portion is dimensioned so that it has a greater cross section than the flexible tube line and the latter can therefore be inserted and removed with play for movement. If an exchange of the flexible tube line is to be carried out, before the old tube line is drawn out, a new tube line can be connected at the rear end of the old tube line by means of an associated connecting element which can likewise be drawn through the supply line and the plug-in socket with play for movement. In this way, when drawing the old tube line out towards the front, the new tube line is simultaneously drawn in from the rear towards the front. All that is required then is the connection of the fitting portion to the front end of the new tube line and the positioning of the fitting portion in the treatment instrument. In this way, a supply line with a defective flexible tube line can be repaired simply and in a cost-favourable manner. It is also possible to remove the flexible tube line merely for the purpose of rinsing and/or sterilizing it in a position remote from the supply line and then to install it again.

The solution according to the invention is suitable in particular for treatment instruments which are realized in two parts and which can be detached from each other by means of a rapid-action coupling or plug-in arrangement. With such a development, the fitting portion which holds and fixes the flexible tube line is located in the rear portion of the treatment instrument which is also suitable for the accommodation of a drive motor for a treatment tool of the treatment instrument.

Features of particular embodiments of the invention further improve the present solution to the problem and lead, moreover, to a simple and cost-effective to manufacture mode of construction which is also practical and rugged, also guaranteeing good sealing.

BRIEF DESCRIPTION OF THE DRAWINGS

The invention and further advantages which can be attained with it are explained in greater detail in the following with the aid of preferred exemplary embodiments and the drawings. In the drawings.

DETAILED DESCRIPTION OF PREFERRED EMBODIMENTS ACCORDING TO THE INVENTION

Figure 1:
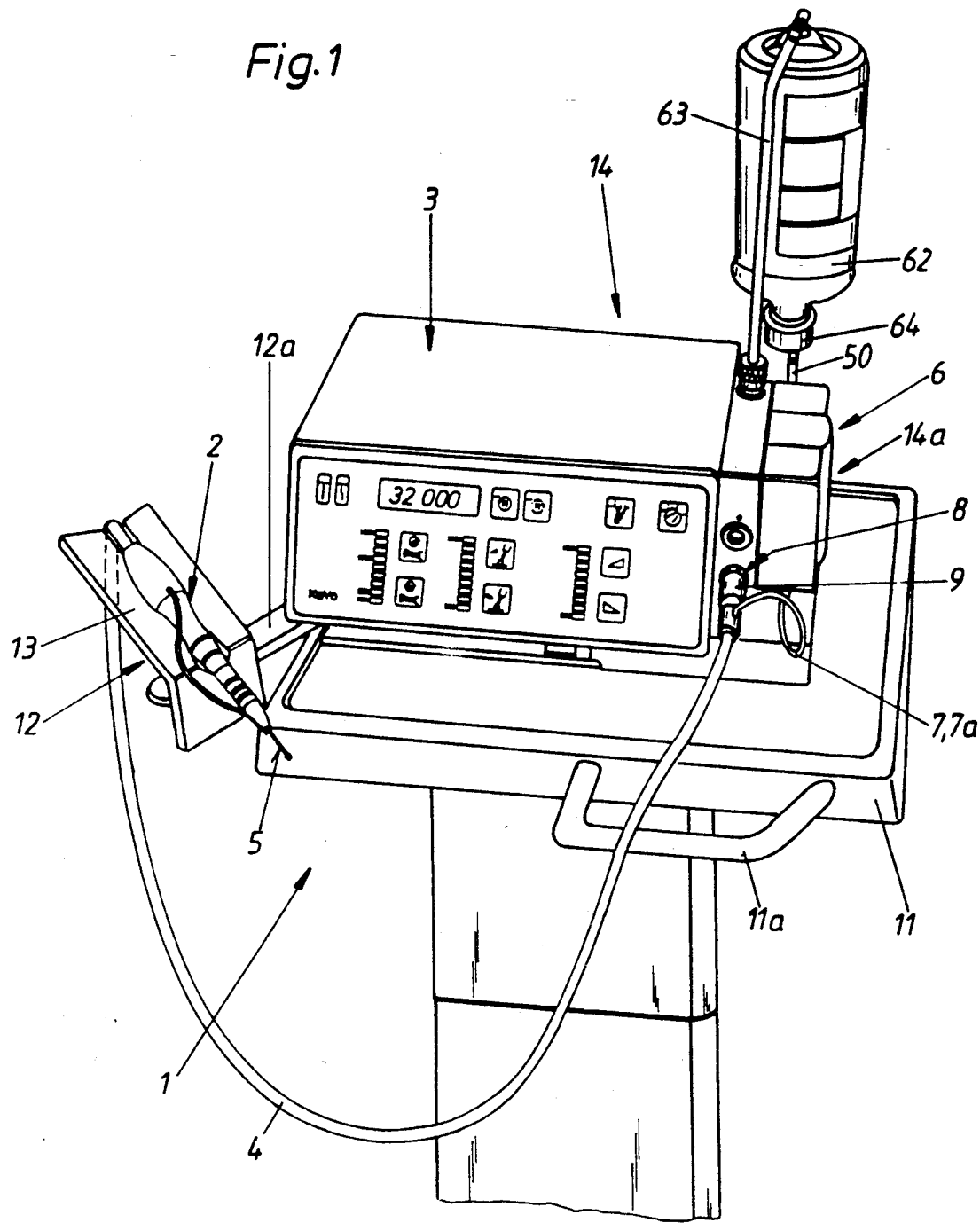
FIG. 1 shows a treatment device, according to the invention, in a perspective representation from the front.
Figure 2:
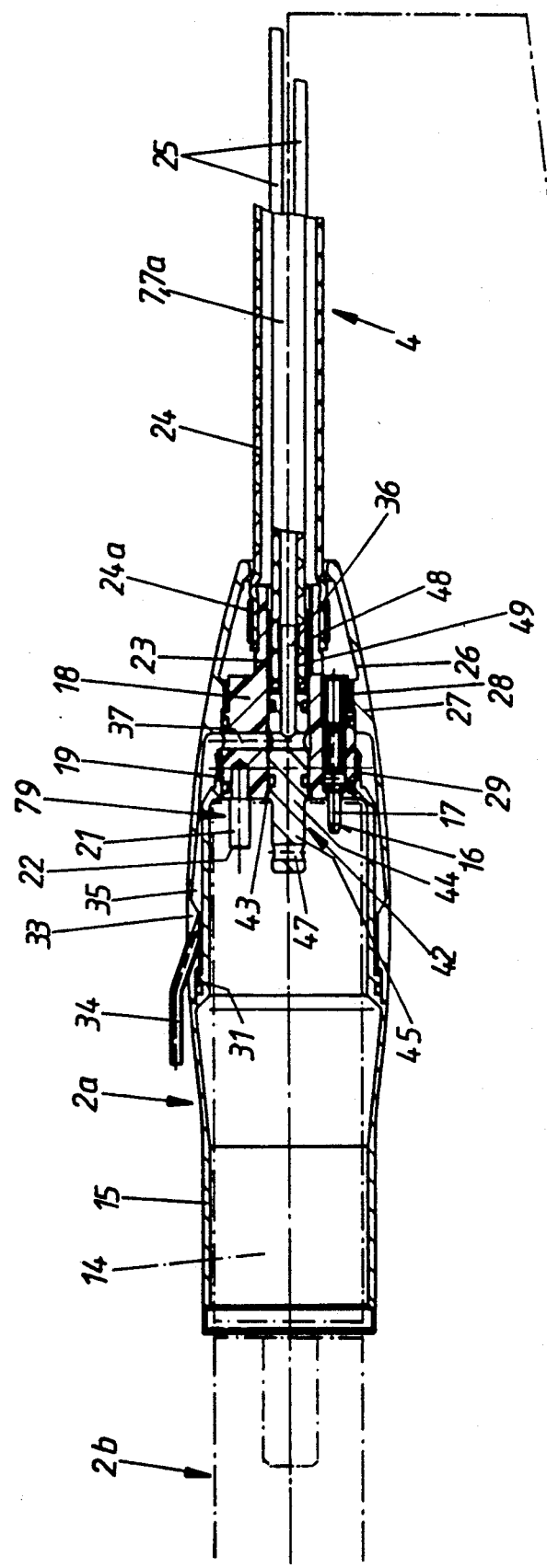
FIG. 2 shows a treatment instrument with associated media supply line in an axial section.
Figure 2:
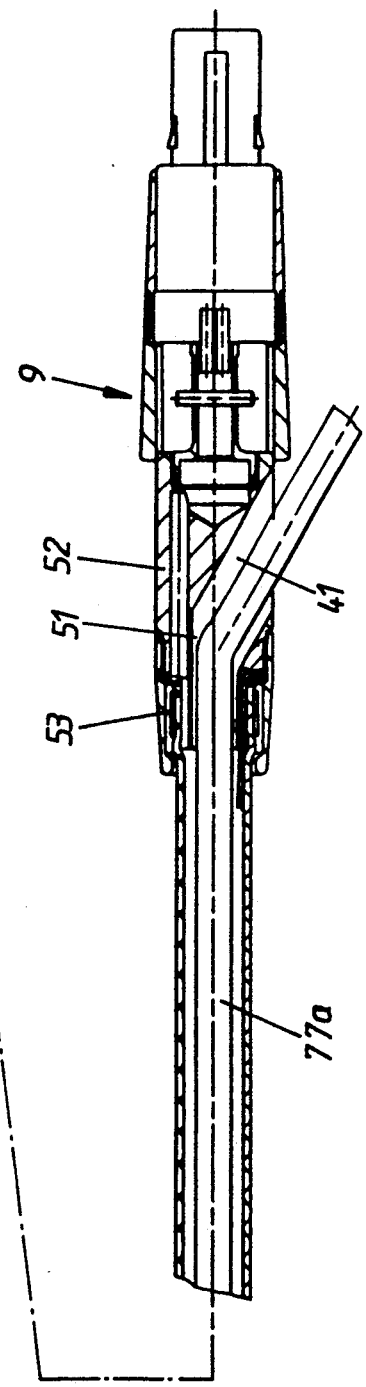

The main portions of the treatment device 1 are the treatment instrument in the form of a hand piece 2 and a control unit 3 with control keys on its front side and with an integrated electronic control device to which the hand piece 2 is connected by means of the bendable or flexible supply line 4. The hand piece 2 bears at its front end a treatment tool 5 which can preferably be exchanged for different, selectively required tools. In the case of such treatment instruments in which the feed of a treatment agent, in particular a cooling fluid such as a salt solution (NaCl), to the treatment position is required, associated with the control unit 3 there is a pump in the form of the hose pump 6 which can preferably be added on to the control unit 3 at the side or can be integrated in said unit. The coolant line 7 which leads to the front end of the hand piece 2 extends at least in part through the supply line 4 and the hand piece 2 respectively. Arranged on the control unit 3 there is a plug-in coupling 8 into which a plug 9, which is arranged at the free end of the supply line 4, can be plugged for the purpose of connection to the electronic control device. For the purpose of positioning the control unit 3, it is possible to provide a frame or table 11 with which a holding arrangement 12 for the hand piece 2, in its standby position, is associated. In the case of the present development, a depository portion is provided in the form of a trough-shaped, oblique plate 13 which is inclined towards the treatment location and on which the hand piece 2 is supported in a form-fitting manner in a position with the tool 5 pointing obliquely downwards. The hand piece 2 is secured against lateral displacement on account of the trough-shaped form of the plate 13. The trough base is preferably adapted to the waisted form of the hand piece 2 so that a form-fitting support also results in the longitudinal direction of the latter. The plate 13 can be held by means of a supporting arm 12a, which projects away from the table 11, or from the housing of the control unit 3, in an approximately horizontal manner, and is mounted thereon preferably so that it can be swung horizontally and the length of which supporting arm 12a is variable, being is freely pivotable at the end of said arm preferably in a joint about an approximately vertical swivel axis.

In order to be able to sterilize the depository portion (plate 13) easily as well, it is advantageous to hold the depository portion by means of a rapid-action coupling or plug-in socket, in particular to arrange it so that it can be plugged in from above, for which purpose a joint pin can be used, which pin can be plugged from above into a joint bore of the supporting arm 12a.

The hand piece 2 consists of two portions which are arranged one after the other in its longitudinal direction, namely a drive portion 2a, which is mounted on the supply line 4, and a work piece carrier portion 2b which can be releasably secured to the drive portion's front end by means of a rapid-action coupling. Arranged in the drive portion 2a there is a suitable drive motor, for example an electric motor or a compressed-air operated turbine motor, which is encapsulated in a housing in the form of a motor cartridge 14 in the manner of a cartouche. The drive portion 2a, for the purpose of accommodating the motor cartridge 14, has a cylindrical sleeve 15 which is open on the front side and the longitudinal dimensions of which are such that it completely covers at least the housing of the motor cartridge 14. Provided on the rear side of the motor cartridge 14 there are two contact elements, preferably lying diametrically opposite each other, in particular in the form of plug-in couplings 16 which correspond with two contact elements in the form of contact pins 17 which protrude from the base of the sleeve parallel to the axis. The contact pins 17 are plugged in a housing insert piece 18 which is round in cross section, sits in an annular collar 19 arranged at the rear end of the sleeve 15 and is secured by means of at least one screw which passes radially in a hole through the rearwardly projecting annular collar 19. The insert piece 18 consists of electrically non-conductive material, in particular plastics material. There projects, moreover, from the insert piece 18 parallel to the axis a positioning pin 21 which fits into a corresponding positioning hole 22 at the rear end of the motor cartridge 14. The positioning pin 21 is arranged so as to be offset in the circumferential direction relative to the contact pins 17 and for the purposes of illustration is displaced into the sectional plane so that only one contact pin 17 is visible. The insert piece 18 has at the rear a tapered cylindrical extension 23 on which a flexible protective hose 24 is plugged and secured by means of a hose clip 24a or the like. There extend in the protective hose 24, according to the embodiment, several conductors, for example two electric cables 25, the cores of which are connected with the contact pins 17 in a manner which is not illustrated, at least one treatment agent hose, in particular coolant hose 7a, and, if applicable, a light guide, all constructed in a flexible manner.

The drive portion 2a has two housing portions which are arranged coaxially relative to each other, namely, on the one hand, the sleeve 15 and a sleeve cap 26 which is at the rear relative to the sleeve and which engages over the rear end region or the rear half of the sleeve 15, covers the insert piece 18 and extends as far as the free end region of the extension 23 where it surrounds the protective hose 24 with play for movement. The sleeve cap 26 has, substantially in its central region, an inner ring extension 27 with a cylindrical inner face 28 which is preferably dimensioned so as to be somewhat smaller in diameter compared with the cylindrical inner face 29 of the ring extension 19. Provided in the rear region of the insert piece 18 between the latter and the ring extension 27 there is an inner thread/outer thread with which the sleeve cap 26 can be screwed on from the rear. The front end of the sleeve cap 26, which is round in cross section, sits on a cylindrical outer ring extension 31 of the sleeve 15 and is sealed by means of a sealing ring (O-ring) which is arranged in a groove preferably in the outer ring extension 31. The inner faces of the ring extension 19 and inner ring extension 27 are also sealed each by means of a respective O-ring which sits in a groove in the insert piece 18. Located behind the front free edge region of the sleeve cap 26 there is a further inner ring extension 33 which is penetrated by a bore which extends obliquely towards the front and outside and in which the rear end of a small tube 34 is inserted in a firm and tight manner, which tube is angled outside the sleeve cap 26 approximately axis-parallel towards the front. Between the outer ring extension 31 and the inner ring extension 27 there extends between the sleeve 15 and the sleeve cap 26 a free annular space 35 from which the small tube 34 issues and which forms a section of the coolant line 7. The latter is connected with the annular space 35 by means of a channel section 36 which extends axially and a channel section 37 which extends radially in the insert piece 18. For the purpose of sealing the plug-in fitting, sealing elements are provided in front of and behind the radial channel section 37, for example O-rings which are arranged in grooves of the fitting cylinder 44.

In the region between the hose pump 6 and the insert piece 18, the coolant line is formed by the coolant hose 7a which is connected to a connection fitting of the hose pump 6, penetrates radially inwards through the plug 9 in a lead-through hole 41 and then extends in the supply line 4 as far as the insert piece 18. Provided for the connection of the coolant hose 7 to the insert piece 18 there is a plug-in spigot 42 which is preferably round and which can be plugged into a coaxial through plug-hole 43 in the insert piece 18 and can be fixed therein in an axial direction in a manner which is not illustrated. The plug-hole 43, in the case of the present development, is a cylindrical through bore hole in which the plug-in spigot 42 can be plugged, with little play, in particular from the front.

The plug-in spigot 42 consists of a fitting cylinder 44 from which there projects a working member 45 in the form of a tapered spigot which in the plugged-in position projects beyond the insert piece 18 towards the front and has a working element preferably in the form of a peripheral groove 47. A recess is provided in the motor cartridge 14 for the accommodation of the working member 45. Pre-formed on the rear side of the fitting cylinder 44 there is a sleeve-like hose nozzle 48 on which the front end of the coolant hose 7a is plugged and is secured by means of a hose clip 49. The radially extending channel section 37 extends in part in the insert piece 18 and in the fitting cylinder 44, with the axial channel section 36 being coaxially arranged in the plug-in spigot 42, running into the hose nozzle 48 at the rear and connecting the coolant hose 7a with the radial channel section 37. The plug-hole 43, the protective hose 24 or its free space respectively and the lead-in hole 41 have such large dimensions in terms of their cross section that the coolant hose 7a, if applicable with hose clip 49, can be guided through with free play. In this connection, the coolant hose 7a must also be set through an axial hole 51 in the rear region of the nozzle 52 of the plug 9 on which the protective hose 24 is clamped with a hose clip 53.

The coolant hose 7a can thus be removed from the supply line 4 quickly, in a simple manner and with ease of handling. For this, it is merely necessary to split up the drive portion 2a and to draw out the motor cartridge 14. With one tool (not illustrated) in the form of a pair of tongs which can be introduced from the front into the sleeve 15, it is possible to grip the working member 45 and draw it with the coolant hose 7a towards the front out of the supply line 4. This can then, if applicable after further disassembly of its individual parts, be steam-sterilized, without the coolant hose 7a, for example in an autoclave at a temperature of approximately 150° C. and a pressure of, for example, 3 bar. The fact that the coolant hose 7a can be removed makes this possible as the latter can be exempted from such stresses of temperature, whereby its life is extended.

In order to install the coolant hose 7a, the latter can either be introduced from the front or from the rear through the lead-through hole 41 into the supply line 4, in which case its connection to the plug-in spigot 42 can be effected beforehand or afterwards.

The last operation of this installation consists in inserting the plug-in spigot 42 with the coolant hose 7a secured thereon from the front into the insert piece 18 into the correct axial position.

It is also possible to exchange the coolant hose 7a in a comparatively simple manner. For this purpose, a new hose 7b is preferably connected to the rear end of the coolant hose 7a by means of a coupling piece which is preferably formed by a connecting pin 54 onto which the pertinent ends of the coolant hoses 7a, 7b can be plugged and secured by means of one common or two hose clips. Subsequently, the old coolant hose 7a can be drawn out towards the front in the previously described manner, with the new coolant hose 7b being drawn in at the same time. After separation of the two hoses 7a, 7b and connection of the new hose 7b to the plug-in spigot 42, the latter with the new hose 7b can then be plugged into its plug-in position in the insert piece 18.

Figure 3:
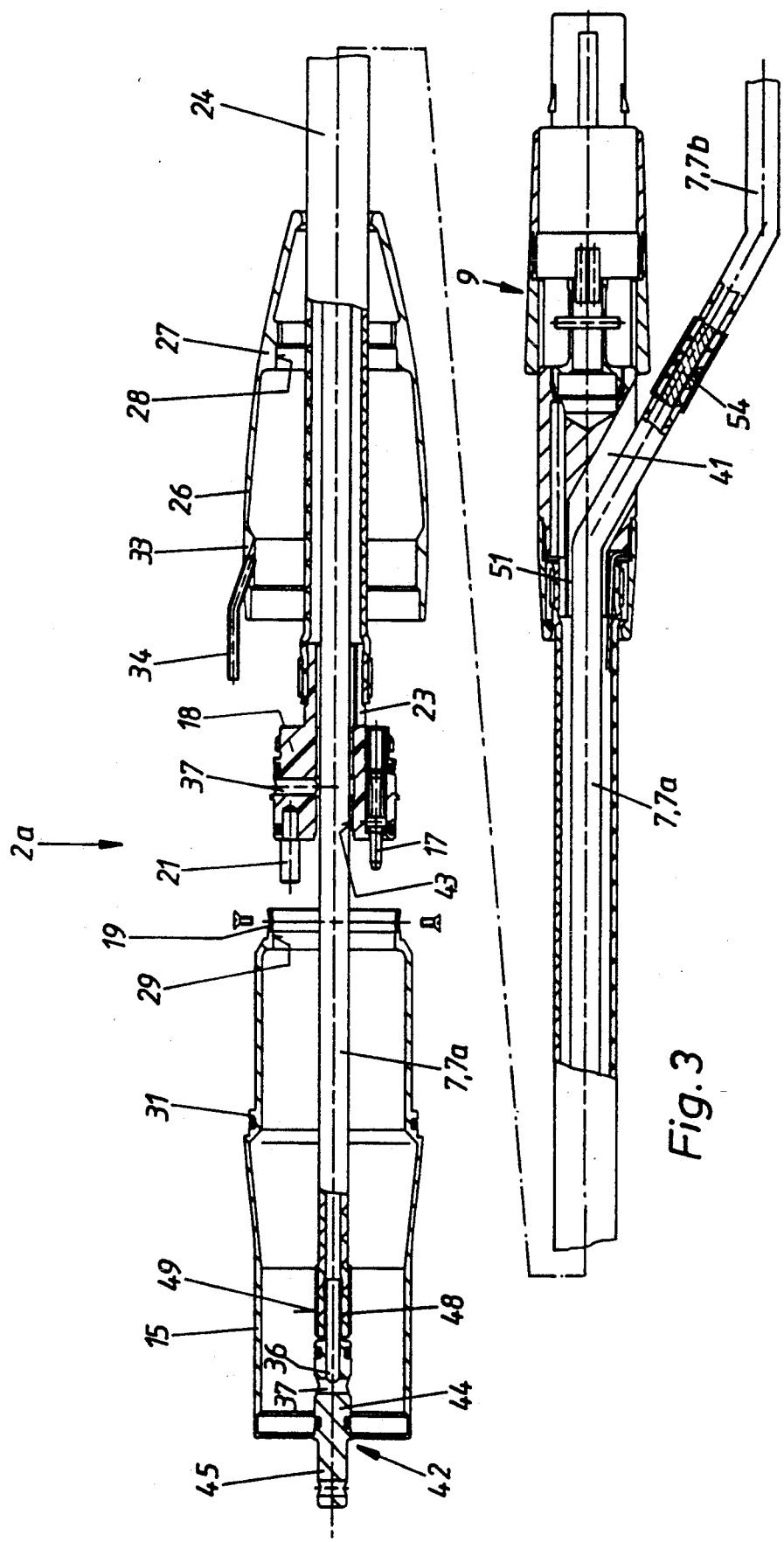
FIG. 3 shows the arrangement according to FIG. 2 in a disassembled position.

For the purpose of further facilitating the installation and removal, it is also possible to detach the sleeve 15 and the rear sleeve cap 26 from each other and separate them from each other so that the insert piece 18 is freely accessible with its working member 25, as represented in FIG. 3.

I claim:

1. A medical treatment device, in particular for surgical purposes, comprising at least one treatment instrument consisting of a handpiece; a control unit; a flexible supply line connecting said handpiece to said control unit, said handpiece including a rear handpiece portion and a front handpiece portion which are releasably interconnected, said rear handpiece portion being connected with the supply line; a source for a treatment agent being operatively associated with said control unit; a treatment agent line being connectable to said source, said treatment agent line including a hose extending at least in part through the supply line to the rear end of the handpiece, said treatment agent line including a hose section which extends at a radial play of movement within the supply line towards the rear handpiece portion; a plug-in spigot having said hose section connected thereto, said spigot being releasably plugged into an axial plug-in socket formed in the rear handpiece portion; an axial channel section of the spigot extending from the hose section and being connected to the treatment agent line so as to be drawable with the hose section towards the front of the handpiece out of the rear handpiece portion.

2. A medical treatment device as claimed in claim 1, wherein said treatment agent comprises a coolant.

3. A treatment device as claimed in claim 1, wherein said treatment agent line comprises hoseless line sections extending within the handpiece.

4. A treatment device as claimed in claim 1, wherein said plug-in spigot is arranged within an insert piece in the handpiece, an axial hole in the handpiece having said insert piece seated therein, and at least one radial channel section of said insert piece which is dimensioned in conformance with the channel section of the plug-in spigot.

5. A treatment device as claimed in claim 4, wherein said plug-in spigot is sealed in the insert piece ahead of and rearwardly of the at least one radial channel section.

6. A treatment device as claimed in claim 5, wherein O-rings seal said plug-in spigot into said insert piece.

7. A treatment device as claimed in claim 4, wherein said plug-in spigot has an attaching member at a front end of said spigot comprising a plug which projects forwardly beyond said plug-in socket.

8. A treatment device as claimed in claim 1, wherein the plug-in spigot includes a connect fitting at a rear end thereof for effecting a releasable connection with said hose.

9. A treatment device as claimed in claim 8, wherein said connect fitting comprises a hose nozzle.

10. A treatment device as claimed in claim 1, wherein the hose in an end region of the supply line remote from the handpiece is guided radially out of the supply line through the intermediary of a lead-through hole and directed obliquely towards the rear, and is releasably connected with the treatment agent source.

11. A treatment device as claimed in claim 4, wherein the supply line includes a protective hose which is connected to the rear end of the insert piece at the rear end of said handpiece.

12. A treatment device as claimed in claim 2, wherein the coolant line includes a second hose section which bridges the separation between said front and rear handpiece portions and is connected by connect fittings with treatment agent line sections extending within the handpiece portions.

13. A treatment device as claimed in claim 4, wherein said rear handpiece portion engages over the front handpiece portion along a section of the length and an annular hollow space between the handpiece portions comprising a part of the treatment agent line and a radial edge section extending into the annular hollow space.

14. A treatment device as claimed in claim 1, wherein said axial channel section extends as a radial channel section and is connected to the treatment agent line.

* * * * *